(12) United States Patent
Bruder et al.

(10) Patent No.: US 9,826,943 B2
(45) Date of Patent: Nov. 28, 2017

(54) METHOD FOR OPERATING A COMPUTER TOMOGRAPHY SYSTEM, AND COMPUTER TOMOGRAPHY SYSTEM

(71) Applicant: Siemens Aktiengesellschaft, Munich (DE)

(72) Inventors: Herbert Bruder, Hochstadt (DE); Thomas Flohr, Uehlfeld (DE)

(73) Assignee: Siemens Aktiengesellschaft, Munich (DE)

( * ) Notice: Subject to any disclaimer, the term of this patent is extended or adjusted under 35 U.S.C. 154(b) by 398 days.

(21) Appl. No.: 14/407,200

(22) PCT Filed: Jun. 3, 2013

(86) PCT No.: PCT/EP2013/061376
§ 371 (c)(1),
(2) Date: Jul. 16, 2015

(87) PCT Pub. No.: WO2013/186073
PCT Pub. Date: Dec. 19, 2013

(65) Prior Publication Data
US 2015/0313556 A1    Nov. 5, 2015

(30) Foreign Application Priority Data
Jun. 11, 2012   (DE) .................. 10 2012 209 692

(51) Int. Cl.
*A61B 6/00*   (2006.01)
*A61B 6/03*   (2006.01)
(Continued)

(52) U.S. Cl.
CPC .............. *A61B 6/032* (2013.01); *A61B 6/027* (2013.01); *A61B 6/03* (2013.01); *A61B 6/4233* (2013.01);
(Continued)

(58) Field of Classification Search
CPC .. A61B 6/00; A61B 6/03; A61B 6/032; A61B 6/4233; A61B 6/52; A61B 6/54; A61B 6/542; A61B 6/544; A61B 6/545; G01N 23/00; G01N 23/046; G01N 23/08; G01N 23/083
(Continued)

(56) References Cited

U.S. PATENT DOCUMENTS 6,266,553 B1   7/2001   Fluhrer et al.
6,408,043 B1   6/2002   Hu et al.
(Continued)

OTHER PUBLICATIONS

GAO, "Medical Imaging Systems," Second Edition (2010).

*Primary Examiner* — Jurie Yun
(74) *Attorney, Agent, or Firm* — Schiff Hardin LLP

(57) ABSTRACT

In a computer tomography system having an x-ray detector with a detector surface at which sensor pixels, for detection of x-ray radiation, are distributed non-uniformly, and a method for operating such a system, either a pitch factor is selected, and a value range for an extent of a reconstruction field for image data is determined dependent on the distribution of the sensor pixels and dependent on the selected pitch factor, or a value for the extent of the reconstruction field is selected, and a value range for the pitch factor is determined dependent on the distribution of the sensor pixels and dependent on the selected value for the extent of the reconstruction field.

11 Claims, 2 Drawing Sheets

(51) Int. Cl.
*A61B 6/02* (2006.01)
*G01T 1/29* (2006.01)
(52) U.S. Cl.
CPC ............... *A61B 6/52* (2013.01); *A61B 6/54* (2013.01); *A61B 6/547* (2013.01); *G01T 1/2985* (2013.01)
(58) Field of Classification Search
USPC .............................................. 378/4, 19, 901
See application file for complete search history.

(56) References Cited

U.S. PATENT DOCUMENTS

| | | |
|---|---|---|
| 6,445,761 B1 | 9/2002 | Miyazaki et al. |
| 6,819,736 B1 | 11/2004 | Bruder et al. |
| 6,870,898 B1 | 3/2005 | von der Haar |
| 6,937,690 B2 | 8/2005 | Bruder et al. |
| 8,031,828 B1 | 10/2011 | DeMan et al. |
| 2003/0068015 A1 | 4/2003 | Bruder et al. |
| 2003/0072419 A1 | 4/2003 | Bruder et al. |
| 2007/0116171 A1 | 5/2007 | Hsieh et al. |

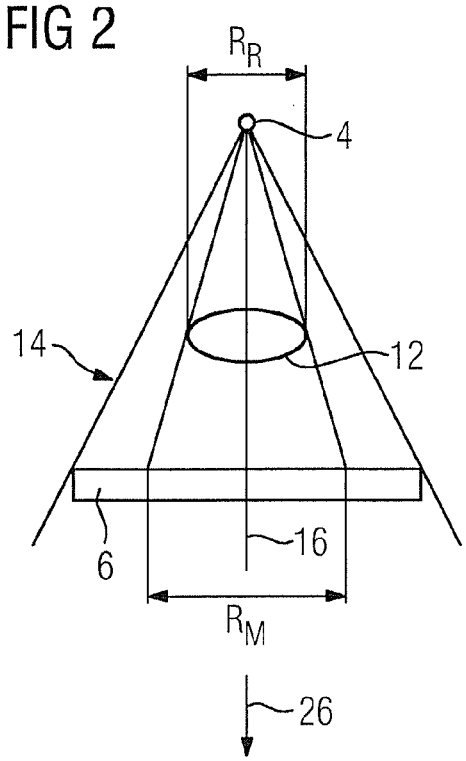
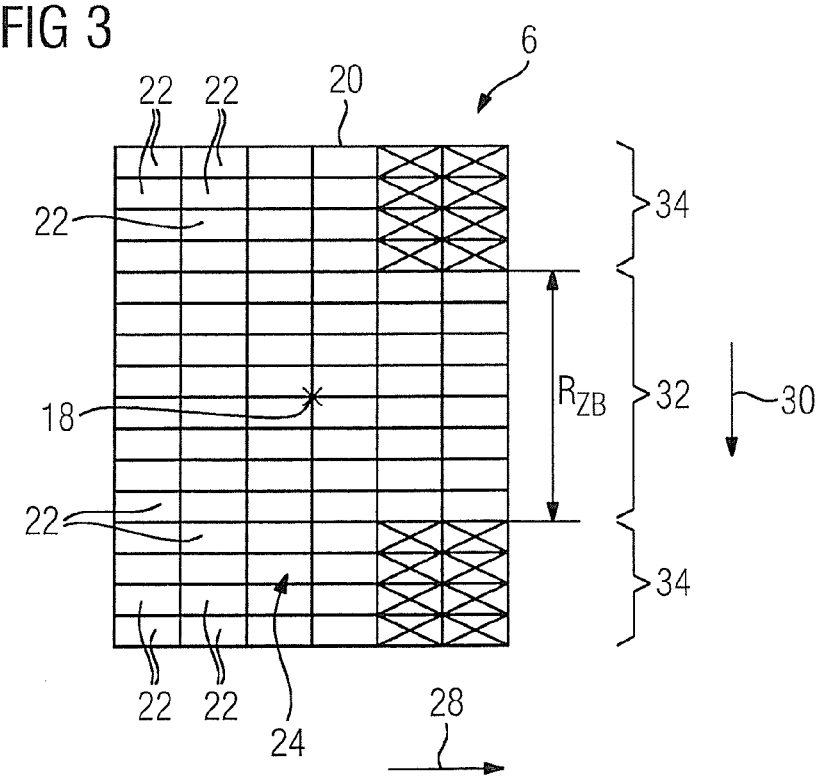

METHOD FOR OPERATING A COMPUTER TOMOGRAPHY SYSTEM, AND COMPUTER TOMOGRAPHY SYSTEM

BACKGROUND OF THE INVENTION

Field of the Invention

The invention concerns a method for operating a computer tomography (also called computed tomography) system that includes an x-ray detector with a detector surface and with a detector middle, and a corresponding computer tomography system.

Description of the Prior Art

In some computer tomography systems, the x-ray detector is positioned in what is known as an asymmetrical partial fan arrangement relative to the x-ray source, as a result of which the center beam of the x-ray fan (which x-ray fan expands conically, emanating from the x-ray source) does not strike the middle of the x-ray detector, but rather strikes offset from the detector middle.

Computer tomography systems with an asymmetrical x-ray detector are also used, for example, as a type known as a T-detector in which detector elements are aligned along a line direction and are also aligned along a channel direction orthogonal to the line direction, wherein the number of detector elements that are aligned in the channel direction decreases as of a defined distance from the detector middle in the line direction.

In both types of computer tomography systems, the available value range for the pitch factor (which indicates the ratio of patient table feed to beam collimation in a type of scan known as a spiral scan, and whose value determines the image quality of the image data that can be generated and the beam exposure of the patient or subject to be examined) is disadvantageously limited.

SUMMARY OF THE INVENTION

On object of the invention is to provide an improved method to operate a computer tomography system, as well as an improved computer tomography system.

The method serves for operating a computer tomography system that includes an x-ray detector with a detector surface and with a detector middle, wherein sensor pixels for detection of x-ray radiation are arranged with non-uniform distribution over the detector surface. In at least one operating mode, either a pitch factor is selected and a value range for the extent of a reconstruction field for the image data preparation is determined depending on the distribution of the sensor pixels over the detector surface and depending on the selected pitch factor, or a value for the extent of the reconstruction field is selected and a value range for the pitch factor is determined depending on the distribution of the sensor pixels over the detector surface and depending on the selected value for the extent of the reconstruction field.

A significant advantage of this method is that, in many usage scenarios for the computer tomography system, a more advantageous and larger value range for the pitch factor can be and is provided to the operator for selection, and the corresponding value range is then adapted to the geometric design of the x-ray detector.

The pitch factor that describes the ratio of table feed of a patient bearing table of the computer tomography system to beam collimation affects the duration of an examination of a patient or of a subject, and affects the beam exposure of the patient or of the subject and the image quality of the image data that can be generated by the computer tomography system. As a result, different aspects are always to be considered in the selection of an advantageous pitch factor for every examination, and accordingly multiple values are to be provided to an operator for selection. An optimally advantageous and optimally large value range is accordingly advantageous. The upper limit of the value range is thereby of particular interest since the duration of an examination typically decreases with increasing value (thus for example given constant slice thickness). An optimally short examination duration is not only advantageous from an economic viewpoint, but also represents an increase in comfort for potential patients. Many patients perceive a corresponding examination by a computer tomography system to be uncomfortable, such that an optimally short examination duration is also desirable from the viewpoint of the patient.

In the following description, a sectional area that intersects the x-ray cone that emanates from the x-ray source of the computer tomography system at the level of the x-ray detector is designated as a detector surface. This sectional area can be covered with the sensor pixels for the sensory detection of the x-ray radiation emanating from the x-ray source. This detector surface is normally limited by the construction design of the computer tomography system. For example, given a computer tomography system with what is known as a gantry, the x-ray source and the x-ray detector are arranged opposing one another on the inner shell surface of a basic hollow cylinder shape, such that as a result the detector surface is also provided by a partial cylindrical shell surface. Its extent in the circumferential direction is limited by the aperture angle of the x-ray cone, and its extent in the middle longitudinal direction of the basic hollow cylinder shape is limited by the extent of the basic hollow cylinder shape (insofar as the x-ray detector projects beyond said basic hollow cylinder shape), by the extent of the x-ray detector or of a mount in this direction and the aperture angle of the x-ray cone.

The detector middle is furthermore to be understood as the position on the x-ray detector at which the middle beam of the beam cone that emanates from the x-ray source strikes at least in an initial bearing. An adjustment capability of the x-ray source and/or of the x-ray detector from an initial alignment is provided in operation, as a result of which a change of the alignment of the x-ray cone relative to the x-ray detector takes place. In this case, the detector middle is also to be understood as a fixed position on the surface of the x-ray detector.

From the extent of the reconstruction field, it is established how the sensors generated by means of the sensor pixels (according to a principle that is known per se) are prepared, and what extent the region of an examined patient or subject has that can ultimately be depicted graphically (thus in slice presentations) with the use of the acquired image data. For example, the extent of the reconstruction field thus determines whether slice presentations of the patient that reproduce the entire width of the patient are available after a spiral scan of the patient, or whether only slice presentations of a kidney of the patient are available.

The detector surface advantageously has a central region with a higher sensor pixel density, positioned around the detector middle, and a border region with a lower sensor pixel density that follows the central region. For example, this is also the case for x-ray detectors of the aforementioned type, such that the method is suitable for a very large range of application scenarios and is also applied in these cases.

In a preferred embodiment of the inventive method, a measurement field at the x-ray detector is associated with the reconstruction field such that the extent of the reconstruction field determines the extent of the measurement field, and wherein an (in particular uniform) base value range with a maximum value for the pitch factor is provided for all values of the extent of the measurement field that are smaller than or equal to the value of the extent of the central region. The measurement field corresponds to a projection of a region in an examination subject which should ultimately be graphically depicted onto the surface of the x-ray detector. The sensor signals of those sensor pixels that lie within the measurement field are then used in order to generate the image data for the graphical depiction. If—as is preferred—a higher sensor pixel density is now present in the central region, and if the extent of the measurement field is smaller than or equal to the extent of the central region, a particularly large value range for the pitch factor (for example of 0.4 to 1.5) is thus provided from which an operator can select.

Furthermore, it is advantageous for the upper limit of the value range for the pitch factor based on the maximum value to be smaller for values of the extent of the measurement field that are greater than the value of the extent of the central region. For the upper limit of the value range, a minimum value (of 0.75, for example) is preferably provided that is established as of a defined extent of the measurement field. The decreasing upper limit for the value range is then the fault of the lower sensor pixel density in the border region, and is specially adapted to this. Instead of thus simply providing a fixed value range with the minimum value as an upper limit, which upper limit is then valid independent of the size of the measurement value is provided accordingly, according to the method proposed here the value range is adapted to the extent of the measurement field so that a more advantageous and larger value range is used depending on the application case.

The adaptation or selection of a matching and advantageous value range for the pitch factor is hereby preferably performed by the operator within the scope of an examination planning in advance of every examination of a patient or subject, wherein at least two branches of a decision tree are provided to the operator as guidelines for selection via a control panel.

In one branch, via the control panel a value range for the pitch factor is provided to the operator, from which value range the operator selects a value via corresponding input. Depending on the selected value, an automatically adapted value range for the extent of the reconstruction field is then provided to the operator, from which the operator then in turn selects a value. The two decision layers do not necessarily need to follow one immediately after the other; additional decision layers in which additional values for additional parameters can be chosen can be present between them. The selection of the values for the additional parameters can then likewise affect the automatic specification of a value range for the extent of the reconstruction field.

In another branch, in contrast to this a value range for the extent of the reconstruction field is initially provided to the operator via the control panel, and after selection of a value from this value range by the operator a value range for the pitch factor is then determined automatically and provided to the operator, at least as a suggestion. In this case as well, additional decision layers can also be provided between these two decision layers, which additional decision layers can likewise affect the automatically provided or at least proposed value range for the pitch factor. The value ranges for the pitch factor and the extent of the reconstruction field are thus linked with one another, and via the two branches it is established which value range is adapted to which selection. A value range is preferably provided such that an operator can merely select values from this value range and make adjustments accordingly within the scope of the examination planning.

Alternatively, only one value range can be proposed and displayed to the operator, without limiting the selection of the actual adjustable values. Given a selection of a value outside of the automatically provided or proposed value range, at least one warning signal is then output (for example as an optical warning signal) via the control panel so that the operator can subsequently restart or correct the examination planning.

However, a method variant is preferable in which the selection of values for the operator is limited, and wherein an automatic adaptation (and in particular a reduction) of the value for the extent of the reconstruction field is conducted upon, for example, a selection by the operator of a value outside of the automatically proposed or provided value range for the pitch factor.

To increase the operating comfort, furthermore an operating mode for the computer tomography system is provided in which—based on a patient diameter that is determined by means of a topogram—a value for the extent of the reconstruction field and, adapted to this, a value range for the pitch factor are provided automatically via the control panel. If a whole-body scan or at least a scan over the entire width of a patient is thus provided, in this case a suitable value for the extent of the reconstruction field is determined automatically in which the image data of a topogram (thus an overview image scan) are evaluated fully automatically.

The above object also is achieved by a computer tomography system in accordance with the invention.

The computer tomography system according to the invention has a control panel and a control unit that is configured to execute the aforementioned method. The computer tomography system preferably has a T-detector with T-shaped sensor pixel distribution. This means that the sensor pixels cover a T-shaped area as viewed in the direction of the middle beam of the x-ray cone. For example, scintillators with downstream photodiodes, or what are known as direct transducers, for example, serve as sensor pixels. The individual sensor pixels are then typically combined into detector units, and multiple detector units form what are known as detector modules.

BRIEF DESCRIPTION OF THE DRAWINGS

FIG. 2 is a side view of the components of the computer tomography system of FIG. 1.

FIG. 3 shows the x-ray detector of the computer tomography system in FIG. 1 in a plan view.

DESCRIPTION OF THE PREFERRED EMBODIMENTS

Figure 1:
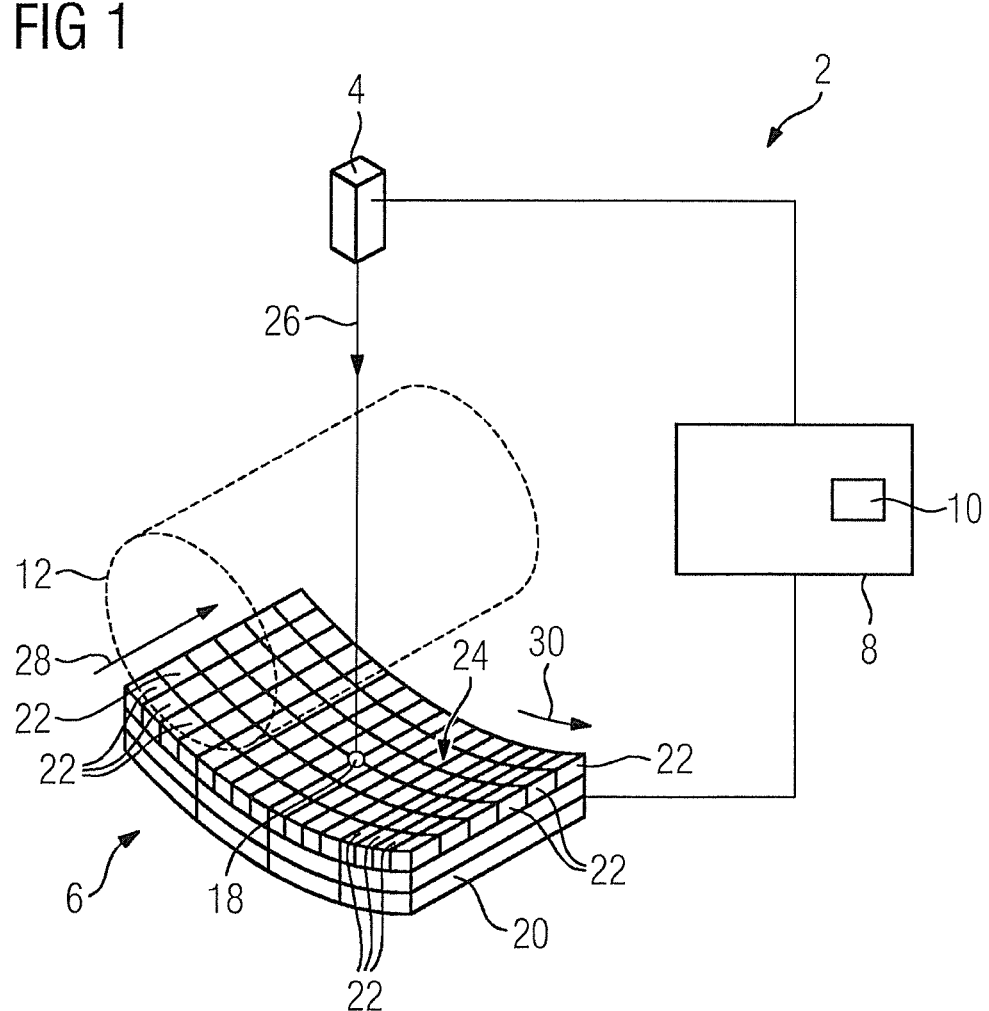
FIG. 1 is a perspective view of a computer tomography system with an x-ray detector.

The exemplary embodiment described in the following and shown in FIG. 1 shows a computer tomography system 2, an x-ray source 4, an x-ray detector 6, a patient support table (not shown in detail) and a control panel 8 with a control unit 10 integrated therein. The computer tomography system 2 serves for examination of patients or examination subjects 12, wherein slice presentations of the examination subject 12 are generated according to a known manner by means of a spiral scan, for example.

With the x-ray source 4, x-ray radiation is generated and emitted in the direction of the x-ray detector 6, wherein an x-ray cone 14 (as indicated in FIG. 2) thereby forms, emanating from the x-ray source 4. Corresponding to a simple geometric consideration, with the x-ray cone 14 a middle beam 16 is provided via which a detector middle 18 is established on the surface of the x-ray detector 6.

The x-ray detector 6 has a base unit 20 into which the detector units 22 can be inserted. Via the constructive design of the base unit 20 that can be populated with detector units 22, in the exemplary embodiment a detector surface 24 is established that is shaped in the manner of a partial cylindrical shell surface of a straight circular cylinder.

As shown in FIG. 3, the detector surface 24 is not completely populated with detector units 22, but rather a portion of the detector surface 24 is left open (unpopulated with detector units) at the edges so that—given a viewing direction in the middle beam direction 26—the detector units 22 cover a T-shaped area. This design is sometimes also referred to as a T-detector. The x-ray detector 6 is thus completely populated in a line direction 28, while the population in a channel direction 30 is incomplete in the line direction 28 as of a certain distance from the detector middle 18. Due to this population, a central region 32 on the x-ray detector 6 is established in which a complete population is provided, as well as a border region 34 following this in the channel direction 30 and in the direction opposite this.

The detector units 22 are similar and are composed of sensor pixels, wherein scintillator crystals with downstream photodiodes and a corresponding readout matrix, or direct transducers, are used as sensor pixels, for example.

If the examination subject 12 should now be examined with a spiral scan, via the control panel 8 an operator starts an examination planning within the framework of which parameter adjustment for the computer tomography system 2 is selected by the operator via the control panel 8, and the actual examination is subsequently started. The examination planning is designed in the manner of a decision tree, wherein the selection of a value for a parameter by the operator in many cases alters the selection of values for other parameters, for example in that the value range from which the operator can select is automatically reduced.

According to the inventive method, the two value ranges, respectively for the pitch factor and the extent of the reconstruction field $R_R$ are linked with one another in this way. The pitch factor—which describes the ratio of table feed of the patient bearing table to beam collimation—can typically also be indicated by the ratio of table feed per rotation of the x-ray detector 6 to the slice thickness of the slice presentations that are to be generated. Since the slice thickness can in most application cases be freely selected only within very narrow limits, ultimately a suitable selection of a value for the table feed often takes place given the selection of a suitable value for the pitch factor.

The extent of the reconstruction field $R_R$ describes the extent of the region of the patient or examination subject 12 that is depicted in the slice presentations generated by the spiral scan. Accordingly, the sensor signals of those sensor pixels that are situated within a measurement field on the surface of the x-ray detector 6 (which measurement field is imaged by projection of the region of the patient or of the examination subject 12 that is to be shown onto the surface of the x-ray detector 6) are of relevance to the preparation of the sensor signals of the sensor pixels to generate the slice presentations. This is shown in FIG. 2. For the selection of adjustable values for the parameters that is offered to the operator within the scope of the examination planning, it is thereby significant whether and to what degree the extent of the measurement field $R_M$ is greater than the extent of the central region $R_{ZB}$. It is assumed that the patient or the examination subject 12 is (as is typical) positioned centrally in the x-ray cone 14 for an examination, and thus is aligned with the middle beam 16.

In many cases, the extent of the reconstruction field $R_R$, and thus the extent of the measurement field $R_M$ that is dependent on this, are predetermined. For example, this is the case if the complete ribcage of a patient should be scanned. In this case, a topogram of the patient is then preferably acquired in advance of the examination planning for the actual examination, and a value for the extent of the measurement field $R_M$ (and thus also a value for the extent of the reconstruction field $R_R$) is determined by an evaluation unit on the basis of the image data of the topogram, which value for the extent of the measurement field $R_M$ is then automatically provided as a preset for the examination planning. If the operator then keeps this preselected value for the subsequent actual examination, as provided the generated slice presentations then image the entire rib cage of the patient. Moreover, the selection of values for the adjustment of the pitch factor is adapted to the preset value for the extent of the reconstruction field $R_R$.

Insofar as the extent of the measurement field $R_M$ (which is dependent on the extent of the reconstruction field $R_{RR}$ [sic]) is smaller than the extent of the central region $R_{ZB}$, a base value range of 0.4 to 1.5 for the pitch factor is provided to the operator. If the extent of the measurement field $R_M$ is greater than the extent of the central region $R_{ZB}$, the value range for the pitch factor from which the operator can select is reduced with increasing extent of the measurement field $R_M$ such that the upper limit of the value range is increasingly reduced. As of a defined extent of the measurement field $R_M$, however, the value range for the pitch factor remains constant, and the upper limit for the pitch factor lies at 0.75 for all extents of the measurement field $R_M$ that are greater than that defined value.

In contrast to this, in some cases a defined value or value range for the pitch factor is provided for a pending examination so that, within the scope of the examination planning, the operator initially adjusts a value for the pitch factor via the control panel 8. In this case, an adaptation of the value range for the extent of the reconstruction field $R_R$ then takes place automatically, from which value range the operator can select and make adjustments for the subsequent examination.

Although modifications and changes may be suggested by those skilled in the art, it is the intention of the inventors to embody within the patent warranted heron all changes and modifications as reasonably and properly come within the scope of their contribution to the art.

We claim as our invention:

1. A method to operate a computer tomography system that comprises an x-ray detector with a detector surface having a detector middle, with sensor pixels for detection of x-ray radiation being distributed non-uniformly over said detector surface, and a control computer that operates said tomography system, including operating said x-ray detector in order to acquire image data, said method comprising:

via an input interface in communication with said control computer, making an entry that is one of either a pitch factor, or a value for an extent of a reconstruction field for said image data detected at said detector surface by said x-ray detector, in order to produce an electronic output from said control computer that controls operation of said x-ray detector for detecting said image data;

in said control computer, when said entry is said pitch factor, automatically selecting a value range for an extent of said reconstruction field dependent on said distribution of said sensor pixels over said detector surface and dependent on said pitch factor, and generating an electronic signal to represent said value range of said extent of said reconstruction field;

in said control computer, when said entry is said value for said extent of said reconstruction field, automatically determining a value range for said pitch factor dependent on said distribution of said sensor pixels over the detector surface and dependent on the entered value for the extent of the reconstruction field, and generating an electronic signal to represent said value range of said pitch factor; and providing the electronic signal that is generated by said control computer from said control computer to an output interface in communication with said control computer, and presenting the value range represented by said electronic signal at a display, prior to operating said x-ray detector in order to acquire said image data.

2. A method as claimed in claim 1 comprising configuring said detector surface with a central region having a first sensor pixel density situated around said detector middle, and a border region, outside of said central region, having a second sensor pixel density, said first sensor pixel density being higher than said second sensor pixel density.

3. A method as claimed in claim 2 comprising providing said x-ray detector with a measurement field associated with said reconstruction field, with said extent of said reconstruction field determining an extent of said measurement field and, in said control computer, providing a base value range with a maximum value for said pitch factor for all values of said extent of said measurement field that are less than or equal to a value of an extent of said central region.

4. A method as claimed in claim 3 comprising, in said control computer, setting an upper limit of the value range for said pitch factor to be smaller, dependent on said maximum value, for values of said extent of said measurement field that are larger than the value of the extent of said central region.

5. A method as claimed in claim 4 comprising, in said control computer, setting a minimum value for said upper limit.

6. A method as claimed in claim 1 comprising:
at said input interface in communication with said control computer, providing a value range for said pitch factor for manual viewing;
receiving, as said value for said pitch factor, a user-selected value from said value range at said input interface; and
in said control computer, automatically determining said value range for the extent of said reconstruction field after selection of said value for said pitch factor from said value range at said input interface.

7. A method as claimed in claim 1 comprising:
at said input interface in communication with said control computer, providing a value range for said extent of said reconstruction field for manual viewing;

receiving, as said value for said extent of said reconstruction field, a user-selected value from said value range at said input interface; and
in said control computer, automatically determining said value range for said pitch factor after selection of said value for said extent of said reconstruction field from said value range at said input interface.

8. A method as claimed in claim 7 comprising, in said control computer, automatically user-selected value of said extent of said reconstruction field if a value thereof selected by said user is outside of a predetermined value range for said extent of said reconstruction field.

9. A method as claimed in claim 1 comprising:
operating said computer tomography system to obtain a topogram of a subject; and
in said control computer, automatically adapting said value for the extent of said reconstruction field and said value range for said pitch factor dependent on said topogram.

10. A computer tomography system comprising
an x-ray detector with a detector surface having a detector middle, with sensor pixels for detection of x-ray radiation being distributed non-uniformly over said detector surface;
a control computer that operates said x-ray detector in order to acquire image data;
a display in communication with said control computer;
an input interface and an output interface each in communication with said control computer;
said control computer being configured to receive, via said input interface, an entry that is one of either a pitch factor, or a value for an extent of a reconstruction field for image data detected at said detector surface by said x-ray detector, and said control computer being configured to produce an electronic output from said control computer in response to said entry that controls operation of said x-ray detector for detecting said image data;
when said entry is said pitch factor, said control computer being configured to automatically select a value range for an extent of said reconstruction field dependent on said distribution of said sensor pixels over said detector surface and dependent on said pitch factor, and to generate an electronic signal to represent said value range of said extent of said reconstruction field;
when said entry is said value for said extent of said reconstruction field, said control computer being configured to automatically determine a value range for said pitch factor dependent on said distribution of said sensor pixels over the detector surface and dependent on the entered value for the extent of the reconstruction field, and to generate an electronic signal to represent said value range of said pitch factor; and
said control computer being configured to provide said electronic signal from said to said said output interface, and to present the value range represented by said electronic signal at said display, prior to operating said x-ray detector in order to acquire said image data.

11. A computer tomography system as claimed in claim 10 wherein said sensor pixel distribution at said detector surface of said x-ray detector is T-shaped.

* * * * *